United States Patent
Tanriover et al.

(10) Patent No.: US 11,006,875 B2
(45) Date of Patent: May 18, 2021

(54) TECHNOLOGIES FOR EMOTION PREDICTION BASED ON BREATHING PATTERNS

(71) Applicant: Intel Corporation, Santa Clara, CA (US)

(72) Inventors: Cagri Tanriover, Bethany, OR (US); Nese Alyuz Civitci, Hillsboro, OR (US); Asli Arslan Esme, Istanbul (TR); Hector Cordourier, Guadalajara (MX); Paulo Lopez Meyer, Zapopan (MX)

(73) Assignee: Intel Corporation, Santa Clara, CA (US)

( * ) Notice: Subject to any disclaimer, the term of this patent is extended or adjusted under 35 U.S.C. 154(b) by 412 days.

(21) Appl. No.: 15/941,435

(22) Filed: Mar. 30, 2018

(65) Prior Publication Data

US 2019/0038201 A1 Feb. 7, 2019

(51) Int. Cl.
*A61B 5/08* (2006.01)
*A61B 5/16* (2006.01)
(Continued)

(52) U.S. Cl.
CPC ............ *A61B 5/165* (2013.01); *A61B 5/0022* (2013.01); *A61B 5/0816* (2013.01);
(Continued)

(58) Field of Classification Search
CPC .... A61B 5/16; A61B 5/00; A61B 5/08; A61B 5/7267; A61B 5/7278; A61B 5/6803;
(Continued)

(56) References Cited

U.S. PATENT DOCUMENTS

| 4,520,238 A | 5/1985 | Ikeda |
| 5,438,980 A | 8/1995 | Phillips |

(Continued)

FOREIGN PATENT DOCUMENTS

| CN | 103156612 | 6/2013 |
| NO | 2017048433 | 3/2017 |

(Continued)

OTHER PUBLICATIONS

Cho, et al. "DeepBreath: Deep Learning of Breathing Patterns for Automatic Stress Recognition using Low-Cost Thermal Imaging in Unconstrained Settings." In proceedings of the 7th International Conference on Affective Computing and Intelligent Interaction, ACII 2017—Preprint: (Year: 2017).*

(Continued)

*Primary Examiner* — Eric J Messersmith
(74) *Attorney, Agent, or Firm* — Hanley, Flight and Zimmerman, LLC

(57) ABSTRACT

Technologies for emotion prediction based on breathing patterns include a wearable device. The wearable device includes a breathing sensor to generate breathing data, one or more processors, and one or more memory devices having stored therein a plurality of instructions that, when executed, cause the wearable device to calibrate a personalized emotion predictive model associated with the user, collect breathing data of the user of the wearable device, analyze the breathing data to determine a breathing pattern, predict, in response to an analysis of the breathing data, the emotional state of the user using the personalized emotion predictive model, and output the emotional state of the user.

25 Claims, 5 Drawing Sheets

(51) Int. Cl.
*A61B 5/00* (2006.01)
*G16H 50/20* (2018.01)
*G16H 40/63* (2018.01)
*G16H 20/70* (2018.01)
*G16H 40/67* (2018.01)
*G16H 50/70* (2018.01)

(52) U.S. Cl.
CPC .......... *A61B 5/4011* (2013.01); *A61B 5/6803* (2013.01); *A61B 5/7267* (2013.01); *A61B 5/7275* (2013.01); *A61B 5/7278* (2013.01); *G16H 20/70* (2018.01); *G16H 40/63* (2018.01); *G16H 40/67* (2018.01); *G16H 50/20* (2018.01); *G16H 50/70* (2018.01)

(58) Field of Classification Search
CPC ..... A61B 5/4011; A61B 5/165; A61B 5/0816; A61B 5/7275; A61B 5/0022; G16H 50/20; G16H 50/70; G16H 40/67; G16H 20/70; G16H 40/63
See application file for complete search history.

(56) References Cited

U.S. PATENT DOCUMENTS

| | | | |
|---|---|---|---|
| 5,986,549 | A | 11/1999 | Teodorescu |
| 6,009,391 | A | 12/1999 | Asghar et al. |
| 6,192,273 | B1 | 2/2001 | Igel et al. |
| 6,290,654 | B1 | 9/2001 | Karakasoglu |
| 6,517,497 | B2 | 2/2003 | Rymut et al. |
| 7,252,640 | B2 | 8/2007 | Ni et al. |
| 8,054,193 | B1 | 11/2011 | Breed et al. |
| 8,636,671 | B2 | 1/2014 | Jang |
| 8,821,415 | B2 | 9/2014 | Al-Ali et al. |
| 2004/0260550 | A1 | 12/2004 | Burges et al. |
| 2006/0064037 | A1 | 3/2006 | Shalon et al. |
| 2006/0079799 | A1 | 4/2006 | Green et al. |
| 2007/0173730 | A1 | 7/2007 | Bikko |
| 2007/0282212 | A1 | 12/2007 | Sierra et al. |
| 2009/0264956 | A1 | 10/2009 | Rise et al. |
| 2011/0066064 | A1 | 3/2011 | Jangle et al. |
| 2011/0071406 | A1 | 3/2011 | Addison et al. |
| 2011/0152707 | A1 | 6/2011 | Jang |
| 2011/0224481 | A1 | 9/2011 | Lee et al. |
| 2011/0295138 | A1 | 12/2011 | Lai et al. |
| 2012/0158620 | A1 | 6/2012 | Paquet et al. |
| 2012/0253216 | A1 | 10/2012 | Fu et al. |
| 2013/0072755 | A1 | 3/2013 | Papania et al. |
| 2013/0226020 | A1 | 8/2013 | Holley et al. |
| 2014/0143064 | A1 | 5/2014 | Tran |
| 2014/0276227 | A1 | 9/2014 | Pérez |
| 2015/0112159 | A1 | 4/2015 | He et al. |
| 2016/0324466 | A1 | 11/2016 | Chang |
| 2016/0361021 | A1 | 12/2016 | Salehizadeh et al. |
| 2017/0078464 | A1 | 3/2017 | Cordourier Maruri et al. |
| 2017/0078788 | A1 | 3/2017 | Lopez Meyer et al. |
| 2017/0086730 | A1 | 3/2017 | Lu et al. |
| 2017/0172459 | A1 | 6/2017 | Bernstein et al. |
| 2017/0273621 | A1 | 9/2017 | Camacho Perez et al. |
| 2018/0199855 | A1 | 7/2018 | Odame et al. |
| 2018/0296125 | A1 | 10/2018 | Zhu et al. |
| 2019/0021633 | A1 | 1/2019 | Wang et al. |
| 2019/0038179 | A1 | 2/2019 | Tanriover et al. |
| 2019/0076643 | A1* | 3/2019 | Siegle .................. A61B 5/0533 |

FOREIGN PATENT DOCUMENTS

| | | |
|---|---|---|
| NO | 2017165028 | 9/2017 |
| TW | 201627815 | 8/2016 |

OTHER PUBLICATIONS

Masaoka, et al., "The effect of anticipatory anxiety on breathing and metabolism in humans," Respiration Physiology 128 (2001) 171-177 (Year: 2001).*

Avalur, "Human Breath Detection using a Microphone," Masters Thesis, University of Groningen, Aug. 30, 2013, 67 pages.
APC International, Ltd., "Piezoelectricity & Wearable Technology: The Future of Piezoelectric Components," Dec. 14, 2016, 5 pages.
Castro et al., "Numerical Simulation of the Performance of a Human Nasal Cavity," Engineering Computations, vol. 28, No. 6, pp. 638-653 (Oct. 27, 2010), 16 pages.
Liu et al., "A Wearable Respiratory Biofeedback System Based on Generalized Body Sensor Network," Telemedicine and e-Health, vol. 17, No. 5, pp. 348-357 (Jun. 2011), 10 pages.
Hult et al., "An Improved Bioacoustic Method for Monitoring of Respiration," Technology and Health Care, vol. 12, pp. 323-332 (2004), 10 pages.
Bosykh et al., "Influence of the Respiratory Cycle Structure on the Flow Field in Human Nasal Cavity at a Fixed Level of Breath Depth," AIP Conference Proceedings (2016), 6 pages.
Lester et al., "Nasal and Oral Inspiration During Natural Speech Breathing," Journal of Speech, Language, and Hearing Research, vol. 57, pp. 734-742 (Jun. 2014), 9 pages.
Moussavi et al., "Breathing Sounds Characteristics Correlate with Structural Changes of Upper Airway due to Dbstructive Sleep Apnea," IEEE, pp. 5956-5959 (2015), 4 pages.
National Heart, Lung, and Blood Institute, "What Controls Your Breathing?" Jul. 17, 2012, available at https://www.nhlbi.nih.gov/health/health-topics/topics/hlw/controls, 1 page (last accessed Jul. 26, 2017).
Medtronic, "Nellcor Bedside Respiratory Patient Monitoring System, PM1000N," 2017, available at http://www.medtronic.com/covidien/products/pulse-oximetry/nellcor-bed, 1 page (last accessed Jul. 26, 2017).
Zheng-Bo et al., "A Wearable Biofeedback System Supporting Real-time Paced Breathing Training and Physiological Monitoring," Biomedical Engineering: Applications, Basis and Communications, vol. 25, No. 2 (Apr. 1, 2013), 2 pages (Abstract only).
Lu et al., "A Semi-Automatic Method for Peak and Valley Detection in Free-Breathing Respiratory Waveforms", Med. Phys. 33(10), pp. 3634-3636 (Oct. 2006), 3 pages.
Daluwatte et al., "A Robust Detection Algorithm to Identify Breathing Peaks in Respiration Signals from Spontaneously Breathing Subjects," Computing in Cardiology, vol. 24, pp. 297-300 (2015), 4 pages.
Curran et al., "Discriminating Between Nasal and Mouth Breathing via Non-Invasive Acoustic Sensors," University of Ulster, available at https://pdfs.semanticscholar.org/b1e4/48da4077999c9598c2308a78c56b309eed6a.pdf (last accessed Aug. 28, 2017), 1 page.
Dash et al., Estimation of Respiratory Rate from ECG, Photoplethysmogram, and Piezoelectric Pulse Transducer Signals: A Comparative Study of Time-Frequency Methods, IEEE Transactions on Biomedical Engineering, vol. 57, No. 5, pp. 1099-1107 (May 2010), 9 pages.
Lee et al., "Irregular Breathing Classification from Multiple Patient Datasets Using Neural Networks," IEEE Transactions on Information Technology in Biomedicine, vol. 16, No. 6, pp. 1253-1264 (Nov. 2012), 12 pages.
Zhdanov et al., "Short Review of Devices for Detection of Human Breath Sounds and Heart Tones," Biology and Medicine, vol. 6, No. 3 (2014), 8 pages.
Lewis, "Understanding Microphone Sensitivity," Analog Dialogue, vol. 46, pp. 1-3 (May 2012), 3 pages.
Gross et al., "The Relationship Between Normal Lung Sounds, Age, and Gender," American Journal of Respiratory and Critical Care Medicine, vol. 162, pp. 905-909 (2000), 5 pages.
"Regulation of Breathing," available at https://media.lanecc.edu/users/driscolln/RT127/Softchalk/regulation_of_Breathing/regulation_of_Breathing.html (last accessed Aug. 30, 2017), 17 pages.
United States Patent and Trademark Office, "Non-Final office action," issued in connection with U.S. Appl. No. 15/669,137, dated Oct. 21, 2019, 17 pages.

(56) References Cited

OTHER PUBLICATIONS

United States Patent and Trademark Office, "Non-Final Office Action," issued in connection with U.S. Appl. No. 15/490,251, dated Apr. 30, 2020, 38 pages.

Abushakra et al., "Acoustic Signal Classification of Breathing Movements to Virtually Aid Breath Regulation," IEEE Journal of Biomedical and Health Informatics, vol. 17, No. 2, Mar. 2013, 8 pages.

Tranulis et al., "Estimation of Pulmonary Arterial Pressure by a Neural Network Analysis Using Features Based on Time-Frequency Representations of the Second Heart Sound," Medical & Biological Engineering & Computing, 2002, 9 pages.

Waldemark et al., "Detection of Apnea Using a Short-Window FFT Technique and an Artificial Neural Network," Proc. SPIE 3390, Applications and Science of Computational Intelligence, Mar. 25, 1998, 13 pages.

United States Patent and Trademark Office, "Final Office Action," issued in connection with U.S. Appl. No. 15/669,137, dated Apr. 16, 2020, 17 pages.

United States Patent and Trademark Office, "Advisory Action," issued in connection with U.S. Appl. No. 15/669,137, dated Jun. 23, 2020, 3 pages.

United States Patent and Trademark Office, "Notice of Allowance," issued in connection with U.S. Appl. No. 15/669,137, dated Jul. 29, 2020, 7 pages.

United States Patent and Trademark Office, "Final Office Action," issued in connection with U.S. Appl. No. 15/819,220, dated Apr. 16, 2020, 21 pages.

United States Patent and Trademark Office, "Non-Final Office Action," issued in connection with U.S. Appl. No. 15/819,220, dated Sep. 18, 2019, 20 pages.

Spire Blog: Respire Relief, "How Does Your Breathing Change When You Feel Tense?" Spire Blog: Respire Relief, Technology for Self-Help, Jul. 9, 2015, 7 pages.

German Patent Office, "Office Action," in connection with German Patent Application No. 102018127776.8, dated Aug. 21, 2019, 24 pages (English Machine Translation Included).

Li et al., "Emotion Recognition from Multi-Channel EEG Data through Convolutional Recurrent Neural Network," 0016 IEEE International Conference on Bioinformatics and Biomedicine (BIBM), 2016, 8 pages.

United States Patent and Trademark Office, "Non-Final Office Action," issued in connection with U.S. Appl. No. 15/660,281, dated Jun. 19, 2019, 39 pages.

United States Patent and Trademark Office, "Non-Final Office Action," issued in connection with U.S. Appl. No. 15/660,281, dated Aug. 6, 2019, 42 pages.

United States Patent and Trademark Office, "Final Office Action," issued in connection with U.S. Appl. No. 15/660,281, dated Feb. 21, 2020, 32 pages.

United States Patent and Trademark Office, "Advisory Action," issued in connection with U.S. Appl. No. 15/660,281, dated May 6, 2020, 4 pages.

United States Patent and Trademark Office, "Advisory Action," issued in connection with U.S. Appl. No. 15/660,281, dated Jun. 22, 2020, 18 pages.

United States Patent and Trademark Office, "Non-Final Office Action," issued in connection with U.S. Appl. No. 15/490,251, dated Dec. 15, 2020, 52 pages.

* cited by examiner

TECHNOLOGIES FOR EMOTION PREDICTION BASED ON BREATHING PATTERNS

BACKGROUND

Bio-signals, such as heart rate and galvanic skin response, have been used to detect valence of an emotion of human subject. For example, changes in respiratory sinus arrhythmia (RSA) have been monitored to detect changes due to emotional variations of human subjects. RSA is defined as the periodic fluctuations in the heart rate related to breathing due to the physical connection between the vagal nerve, the lungs, the heart, as well as with the other organs. As such, metabolic activities and/or individual differences in bio-signals may affect detecting valence of an emotion of a human subject.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
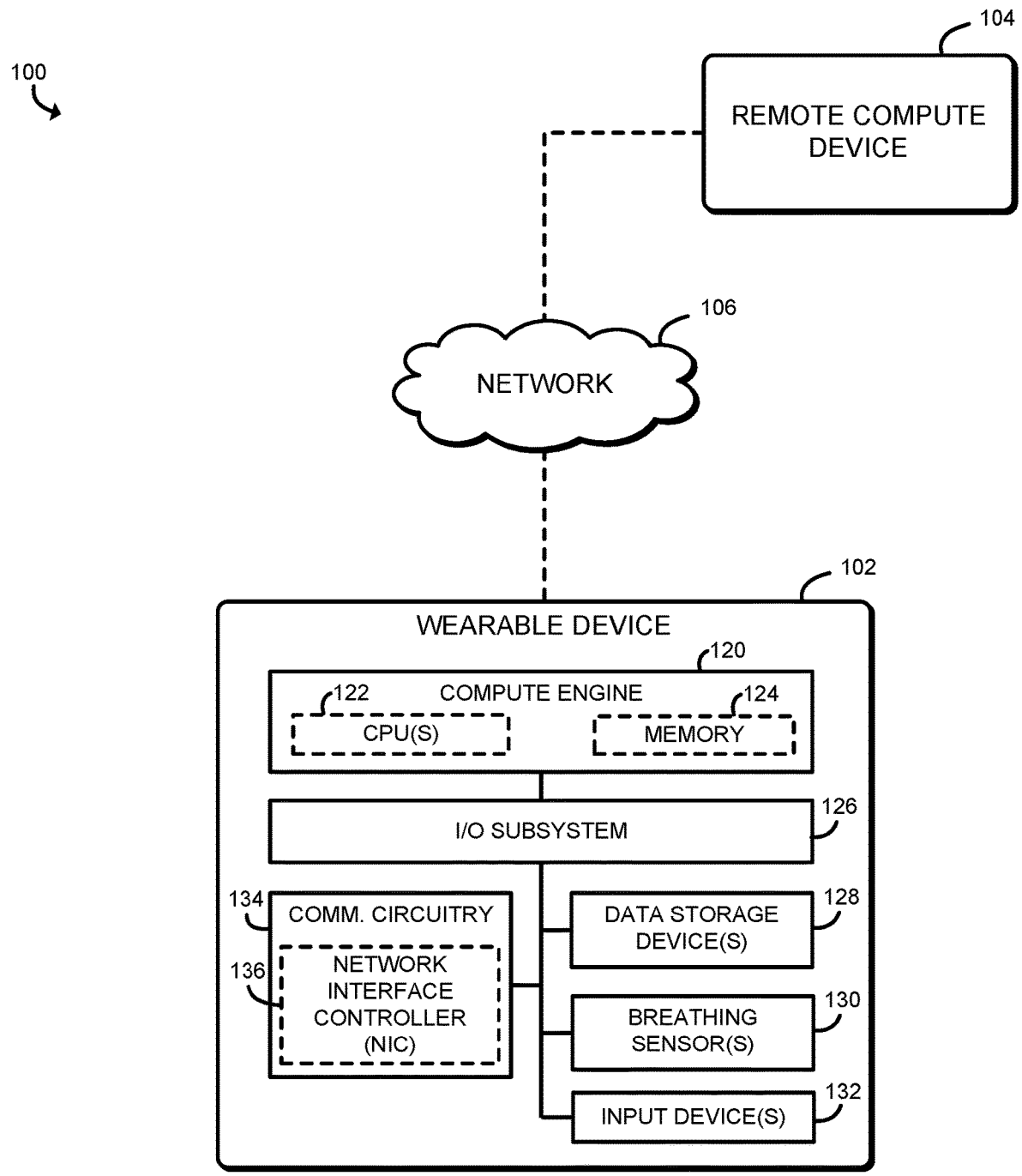
FIG. 1 is a simplified block diagram of at least one embodiment of a system for classifying breathing patterns to predict an emotional state of a user of the wearable device.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, an illustrative system 100 for classifying breathing patterns to predict an emotional state of a user of the wearable device 102 is shown. In use, as described further below, the wearable device 102 may collect and analyze the breathing data of the user of the wearable device 102. The breathing data includes four phases of a breathing cycle: inspiration ($T_{ip}$), inspiration pause ($T_{ip}$), expiration ($T_e$), and expiration pause ($T_{ep}$). For example, the average time periods for the breathing phases during typical breathing for the inspiration phase ($T_i$) is about 2.58 seconds, the inspiration pause phase ($T_{ip}$) is about 0.23 seconds, the expiration phase ($T_e$) is about 1.72 seconds, and the expiration pause phase ($T_{ep}$) is about 2.13 seconds. The wearable device 102 may further extract one or more breathing patterns based on breathing pattern metrics. For example, the breathing pattern metrics may include, among other things, a ratio between inspiration and expiration durations ($T_i/T_e$), a respiration frequency ($f_R = 1/(T_i + T_{ip} + T_e + T_{ep})$), and/or ratios that indicate each phase of the respiration cycle compared to the total respiration duration ($T_i * f_R$, $T_e * f_R$, $T_{ip} * f_R$, $T_{ep} * f_R$). The extracted breathing pattern(s) and the time periods for the breathing phases may be used as inputs to an emotion predictive model to predict an emotional state (e.g., valence and arousal levels) of the user.

Since the breathing patterns may be highly dependent on the user of the wearable device 102, the emotion predictive model may be calibrated to generate a personalized emotion predictive model for the user. To do so, prior to predicting the emotional state of the user, several scents may be sequentially exposed to the user to collect training breathing data to extract a breathing pattern for each scent. In addition to extracting breathing patterns, the user may also provide a self-labeled class associated with each scent. For example, the user may provide a valence level (e.g., negative, neural, or positive) and/or an arousal level (e.g., low, medium, or high) associated with each scent. The wearable device 102 may associate the extracted breathing patterns with the corresponding self-labeled classes to train a personalized emotion predictive model that is specifically tailored to the user. Subsequently, the wearable device 102 may utilize the personalized emotion predictive model associated with the user to predict an emotional state of the user based on breathing data.

Referring back to FIG. 1, the wearable device 102 may be embodied as any type of device, structure, or system having various aspects or characteristics capable of performing the functions described herein. The wearable device 102 may be embodied as smart eyeglasses or any other form factor for an electronic device that may be worn by a user. As shown in FIG. 1, the illustrative wearable device 102 includes a compute engine 120, an input/output ("I/O") subsystem 126, one or more data storage devices 128, one or more breathing sensors 130, one or more input devices 132, and communication circuitry 134 which may further include a network interface controller (NIC) 136. It should be appreciated that, in some embodiments, the wearable device 102 may include other or additional components, such as those commonly found in a typical computing device (e.g., various input/output devices and/or other components). Additionally, in some embodiments, one or more of the illustrative components may be incorporated in, or otherwise form a portion of, another component.

The compute engine 120 may be embodied as any type of device or collection of devices capable of performing the various compute functions as described below. In some embodiments, the compute engine 120 may be embodied as a single device such as an integrated circuit, an embedded system, a field-programmable-array (FPGA), a system-on-a-chip (SoC), an application specific integrated circuit (ASIC), reconfigurable hardware or hardware circuitry, or other specialized hardware to facilitate performance of the functions described herein. Additionally, in some embodiments, the compute engine 120 may include, or may be embodied as, one or more CPUs 122 and memory 124. The CPU 122 may be embodied as any type of processor capable of performing the functions described herein. For example, the CPU 122 may be embodied as a single or multi-core processor(s), digital signal processor, microcontroller, or other processor or processing/controlling circuit.

The memory 124 may be embodied as any type of volatile or non-volatile memory or data storage capable of performing the functions described herein. In operation, the memory 124 may store various data and software used during operation of the wearable device 102 such as applications, programs, libraries, and drivers. The memory 124 is communicatively coupled to the CPUs 122 via the I/O subsystem 126, which may be embodied as circuitry and/or components to facilitate input/output operations with the CPUs 122, the memory 124, and other components of the wearable device 102. For example, the I/O subsystem 126 may be embodied as, or otherwise include, memory controller hubs, input/output control hubs, integrated sensor hubs, firmware devices, communication links (e.g., point-to-point links, bus links, wires, cables, light guides, printed circuit board traces, etc.), and/or other components and subsystems to facilitate the input/output operations. In some embodiments, the I/O subsystem 126 may form a portion of a system-on-a-chip (SoC) and be incorporated, along with one or more of the CPU 122, the memory 124, and other components of the wearable device 102, on a single integrated circuit chip.

The data storage device(s) 128 may be embodied as any type of device or devices configured for short-term or long-term storage of data such as, for example, memory devices and circuits, memory cards, hard disk drives, solid-state drives, or other data storage devices. In some embodiments, the data storage device(s) 128 may form a portion of the memory 124. In the illustrative embodiment, the wearable device 102 may be configured to store breathing data, user-specific class labeled data, and a personalized emotion predictive model in the data storage device(s) 128.

The breathing sensor(s) 130 may be embodied as any type of sensor capable of measuring breathing of a user of the wearable device 102 and producing breathing data indicative of breathing pattern of the user. For example, in the illustrative embodiment, the breathing sensor(s) 130 may be embodied as, or otherwise include, one or more piezoelectric (PZ) sensors, such as piezoelectric diaphragms. In the illustrative embodiment, the piezoelectric sensors may be positioned proximate to the nose (e.g., a bridge of a nose) of a user wearing the wearable device 102 to detect the vibration of the nasal bridge as the user breathes in and out of the user's nose and/or mouth. The piezoelectric sensors may be configured to produce sensor data by converting vibration into electrical signals (i.e., the breathing data). It should be appreciated that, in some embodiments, the breathing sensor(s) 130 may be embodied as any type of sensor that can measure vibrations at other portions of the user's body (e.g., the user's temples, forehead, chest, or abdomen).

The input device(s) 132 may be embodied as any type of device capable of receiving an input from a user of the wearable device 102. For example, in some embodiments, the input device(s) 132 may include a touch screen, graphics circuitry, keyboard, and/or interface devices capable of receiving an input from a user of the wearable device 102. In use, the input device(s) 132 is configured to receive a self-labeled class from a user of the wearable device 102 indicating a valence level (e.g., negative, neural, or positive) and/or an arousal level (e.g., low, medium, or high) for each testing scent that was exposed to the user during calibration of the personalized emotion predictive model. Although the input device(s) 132 is shown as a subcomponent of the wearable device 102, in some embodiments, one or more input devices 132 may be communicatively or wirelessly coupled to the wearable device 102 via the communication circuit 134.

The communication circuit 134 may be embodied as any type of communication circuit, device, or collection thereof, capable of enabling communications to and from the wearable device 102. To do so, the communication circuit 134 may be configured to use any one or more communication technologies (e.g., wireless or wired communications) and associated protocols (e.g., ANT, ZIGBEE, Ethernet, Bluetooth®, Wi-Fi®, WiMAX, LTE, 4G, 5G, etc.) to effect such communication. In some embodiments, the communication circuit 134 may transmit breathing data generated by the breathing sensors 130 to a remote compute device 104 for further processing.

In other embodiments, the breathing sensors 130 may be wirelessly coupled to the wearable device 102. In such embodiments, the communication circuit 134 may enable communications between the wearable device 102 and the breathing sensors 130 to receive breathing data from the breathing sensors 130. Moreover, in some embodiments, one or more input devices 132 may be communicatively coupled to the wearable device 102. In such embodiments, the communication circuit 134 may enable communications between the wearable device 102 and the input device 132. Additionally or alternatively, in other embodiments, one or more input devices 132 may be coupled to the remote compute device 104. In such embodiments, the communication circuit 134 may enable communications between the wearable device 102 and the remote compute device 104 via a network 106.

The remote compute device 104 may be embodied as a cellular phone, a mobile computing device, a tablet, a computer, a server, a computation device, a networked device, a distributed compute system, or other device capable of receiving communications from the wearable device 102 via the network 106. Thus, the remote compute device 104 may include a compute engine, an I/O subsystem, a data storage device, communication circuitry, and/or other components and devices commonly found in a smartphone or similar computing device. The individual components of the remote compute device 104 may be similar to the corresponding components of the wearable device 102, the description of which is not repeated herein so as not to obscure the present disclosure.

As discussed above, the system 100 may include the network 106. The network 106 may be embodied as any type of network capable of facilitating communications between the wearable device 102 and the remote compute device 104. For example, the network 106 may be embodied as, or otherwise include, a wireless local area network (LAN), a wireless wide area network (WAN), a cellular network, and/or a publicly-accessible global network such as the Internet. As such, the network 106 may include any number of additional devices, such as one or more input devices, additional computers, routers, and switches, to facilitate communications thereacross.

Figure 2:
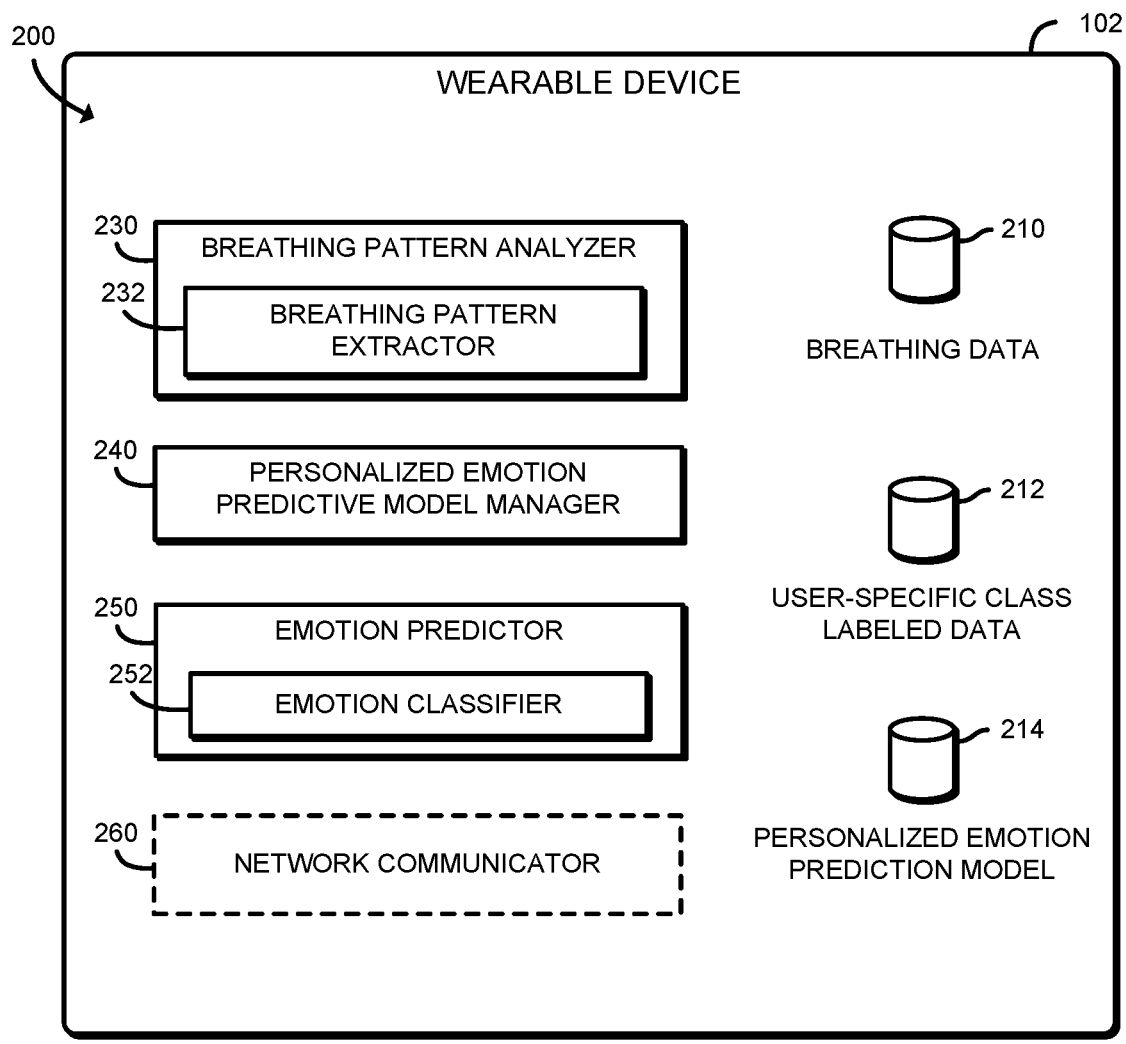
FIG. 2 is a simplified block diagram of at least one embodiment of an environment that may be established by a wearable device of FIG. 1.

Referring now to FIG. 2, in use, the wearable device 102 establishes an environment 200 for classifying breathing patterns to predict an emotional state of a user of the wearable device 102. The illustrative environment 200 includes a breathing pattern analyzer 230, a personalized emotion predictive model manager 240, an emotion predictor 250, and, in some embodiments, a network communicator 260. The breathing pattern analyzer 230 further includes a breathing pattern extractor 232, and the emotion predictor 250 further includes an emotion classifier 252. The illustrative environment 200 further includes breathing database 210, user-specific class labeled database 212, and personalized emotion prediction model database 214. The various components of the environment 200 may be embodied as hardware, firmware, software, or a combination thereof. As such, in some embodiments, one or more of the components of the environment 200 may be embodied as circuitry or collection of electrical devices (e.g., breathing pattern analyzer circuitry 230, breathing pattern extractor circuitry 232, personalized emotion predictive model manager circuitry 240, emotion predictor circuitry 250, emotion classifier circuitry 252, network communicator circuitry 260, etc.). It should be appreciated that, in such embodiments, one or more of the breathing pattern analyzer circuitry 230, the breathing pattern extractor circuitry 232, the personalized emotion predictive model manager circuitry 240, the emotion predictor circuitry 250, the emotion classifier circuitry 252, and/or the network communicator circuitry 260 may form a portion of one or more of the compute engine 120, the I/O subsystem 126, the communication circuit 134, and/or other components of the wearable device 102. Additionally, in some embodiments, one or more of the illustrative components of the environment 200 may form a portion of another component and/or one or more of the illustrative components may be independent of one another.

The breathing pattern analyzer 230 is configured to analyze breathing data collected from the breathing sensors 130 to determine one or more breathing patterns. It should be appreciated that the breathing data is stored in the breathing database 210. To do so, the wearable device 102 includes the breathing pattern analyzer 230. In the illustrative embodiment, the wearable device 102 is configured to identify the breathing phases based on the breathing data and determine the breathing phase time periods for the breathing phases. Using the breathing phase time periods, the breathing pattern extractor 232 is configured to determine the breathing pattern based on one or more breathing pattern metrics. As discussed above, the breathing pattern metrics may include, among other things, a ratio between inspiration and expiration durations ($T_i/T_e$), a respiration frequency ($f_R=1/(T_i+T_{ip}+T_e+T_{ep})$), and/or ratios that indicate each phase of the respiration cycle compared to the total respiration duration ($T_i*f_R$, $T_e*f_R$, $T_{ip}*f_R$, $T_{ep}*f_R$). As discussed in detail below, the breathing patterns may be used to calibrate a personalized emotion prediction model of the user and/or predict an emotional state of the user.

The personalized emotion predictive model manager 240 is configured to generate a personalized emotion predictive model associated with the user of the wearable device 102. It should be appreciated that the personalized emotion prediction model is embodied as a mathematical model or algorithm that takes breathing patterns and breathing phase time periods extracted from breathing data as inputs and produces a predicted emotional state of the user of the wearable device 102. As discussed above, the breathing pattern varies depending on the user of the wearable device 102. As such, the personalized emotion predictive model manager 240 is configured to generate a personalized emotion prediction model that is specifically tailored to the user of the wearable device 102. To generate and train the personalized emotion prediction model in the illustrative embodiment, several testing scents may be sequentially exposed to the user to collect training breathing data for each scent. In response, the personalized emotion predictive model manager 240 is configured to receive an extracted breathing pattern for each scent from the breathing pattern extractor 232. Additionally, the personalized emotion predictive model manager 240 is configured to receive a self-labeled class associated with each scent from the user. For example, the user may provide a valence level (e.g., negative, neural, or positive) and/or an arousal level (e.g., low, medium, or high) associated with each scent. Based on the breathing patterns and the user-specific class labeled data, the personalized emotion predictive model manager 240 is configured to train the personalized emotion prediction model using one or more machine learning algorithms to classify breathing patterns. The resulting personalized emotion predictive model is stored in the personalized emotion prediction model database 214 to be used by the emotion predictor 250.

The emotion predictor 250, which may be embodied as hardware, firmware, software, virtualized hardware, emulated architecture, and/or a combination thereof as discussed above, is configured to predict an emotional state of the user of the wearable device 102 using the personalized emotion predictive model of the user. To do so, the emotion predictor 250 includes the emotion classifier 252. The emotion classifier 252 is configured to classify one or more extracted breathing patterns using the personalized emotion predictive model based on the breathing pattern metrics and the breathing phase time periods ($T_i$, $T_e$, $T_{ip}$, $T_{ep}$). The emotion predictor 250 is further configured to output a predicted emotional state of the user of the wearable device 102. For example, the emotion predictor 250 outputs a valence level (e.g., negative, neural, or positive) and/or an arousal level (e.g., low, medium, or high) of the user of the wearable device 102.

The network communicator 260, which may be embodied as hardware, firmware, software, virtualized hardware, emulated architecture, and/or a combination thereof as discussed above, is configured to facilitate inbound and outbound network communications to and from the wearable device 102, respectively. For example, in some embodiments, the network communicator 260 may transmit breathing data to the remote compute device 104 for a determination of a predicted emotional state of the user and may receive a predicted emotional state from the remote compute device 104. In other embodiments, the network communicator 260 may transmit a predicted emotional state determined by the emotion predictor 250 to the remote compute device 104. Accordingly, in some embodiments, at least a portion of the functionality of the network communicator 260 may be performed by the communication circuitry 134.

Figure 3:
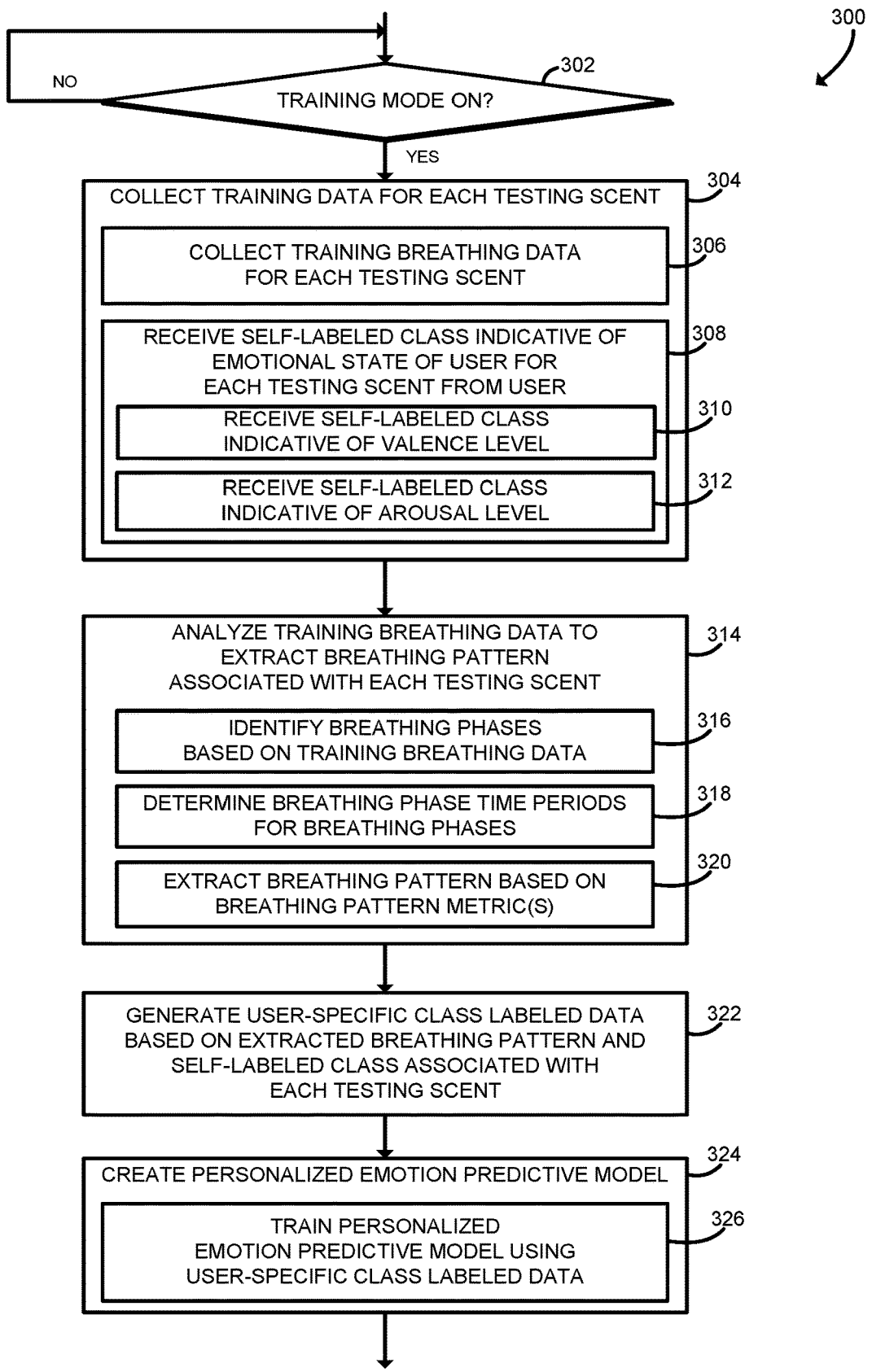
FIG. 3 is a simplified flow diagram of at least one embodiment of a method for training a personalized emotion predictive model using machine learning that may be executed by the wearable device of FIGS. 1 and 2.

Referring now to FIG. 3, in use, the wearable device 102 may execute a method 300 for calibrating the wearable device 102 to generate a personalized emotion predictive model for a user of the wearable device 102. The method 300 begins with block 302 in which the wearable device 102 determines whether a training mode of the wearable device 102 is activated. For example, the training mode may be activated to create a personalized emotion predictive model for a new user of the wearable device 102. Alternatively, the training mode may be activated to update an existing personalized emotion predictive model for an existing user of the wearable device 102. If the wearable device 102 determines that the training mode is not activated, the method 300 loops back to block 302 to continue monitoring for an activation of the training mode of the wearable device 102. If, however, the wearable device 102 determines that the training mode is activated, the method 300 advances to block 304.

During the training mode in block 304, the user of the wearable device 102 is exposed to various testing scents. For each testing scent, the wearable device 102 collects training breathing data from the breathing sensors 130 as indicated in block 306. Additionally, for each testing scent, the wearable device 102 receives a corresponding self-labeled class from the user via one or more input devices 132 in block 308. The self-labeled class indicates an emotional state of the user via the input device(s) 132. For example, in the illustrative embodiment, the emotional state may include a valence level (e.g., negative, neural, or positive) and an arousal level (e.g., low, medium, or high). As such, the wearable device 102 receives a self-labeled class indicative of a valence level and an arousal level associated with each scent from the user in blocks 310 and 312, respectively.

In block 314, the wearable device 102 analyzes the training breathing data to determine a breathing pattern associated with each testing scent. To do so, in block 316, the wearable device 102 identifies the breathing phases based on the training breathing data. As discussed above, the breathing phases include inspiration ($T_i$), inspiration pause ($T_{ip}$), expiration ($T_e$), and expiration pause ($T_{ep}$) phases. For each of the breathing phases, the wearable device 102 determines a corresponding breathing phase time period as indicated in block 318.

In block 320, the wearable device 102 extracts a breathing pattern based on one or more breathing pattern metrics for each scent. As discussed further below, the breathing pattern is one of feature vectors that is used to train a machine learning model (i.e., a personalized emotion predictive model). It should be appreciated that the breathing pattern may include multiple values and may further include other features extracted from the breathing data. For example, the breathing pattern metrics may include a ratio between inspiration and expiration durations ($T_i/T_e$), a respiration frequency ($f_R=1/(T_i+T_{ip}+T_e+T_{ep})$), and/or ratios that indicate each phase of the respiration cycle compared to the total respiration duration ($T_i*f_R$, $T_e*f_R$, $T_{ip}*f_R$, $T_{ep}*f_R$). Typically, the breathing pattern varies depending on how the user of the wearable device 102 perceives the corresponding scent. As such, the breathing pattern may indicate whether a scent is pleasant or unpleasant to the user of the wearable device 102.

In block 322, the wearable device 102 generates a user-specific class labeled data based on the extracted breathing pattern and the self-labeled class associated with each testing scent. In other words, the user-specific class labeled data associates the user-labeled class with the corresponding breathing pattern.

In block 324, the wearable device 102 creates a personalized emotion predictive model using the user-specific class labeled data. To do so, the personalized emotion predictive model is trained using one or more machine learning algorithms to classify breathing patterns based on the user-specific class labeled data as indicated in block 326. As such, the personalized emotion predictive model is specifically tailored to the current user of the wearable device 102. It should be appreciated that, in some embodiments, the wearable device 102 may update and calibrate the existing personalized emotion predictive model of the user using more training breathing data.

As discussed above, in some embodiments, method 300 may be executed by the remote compute device 104 to create a personalized emotion predictive model. To do so, the training breathing data may be transmitted to a remote compute device 104 via the network 106. In such embodiments, the personalized emotion predictive model may be stored at the remote compute device 104 for future analysis. Alternatively, the personalized emotion predictive model may be transmitted to the wearable device 102 for implementation for further analysis.

Figure 4:
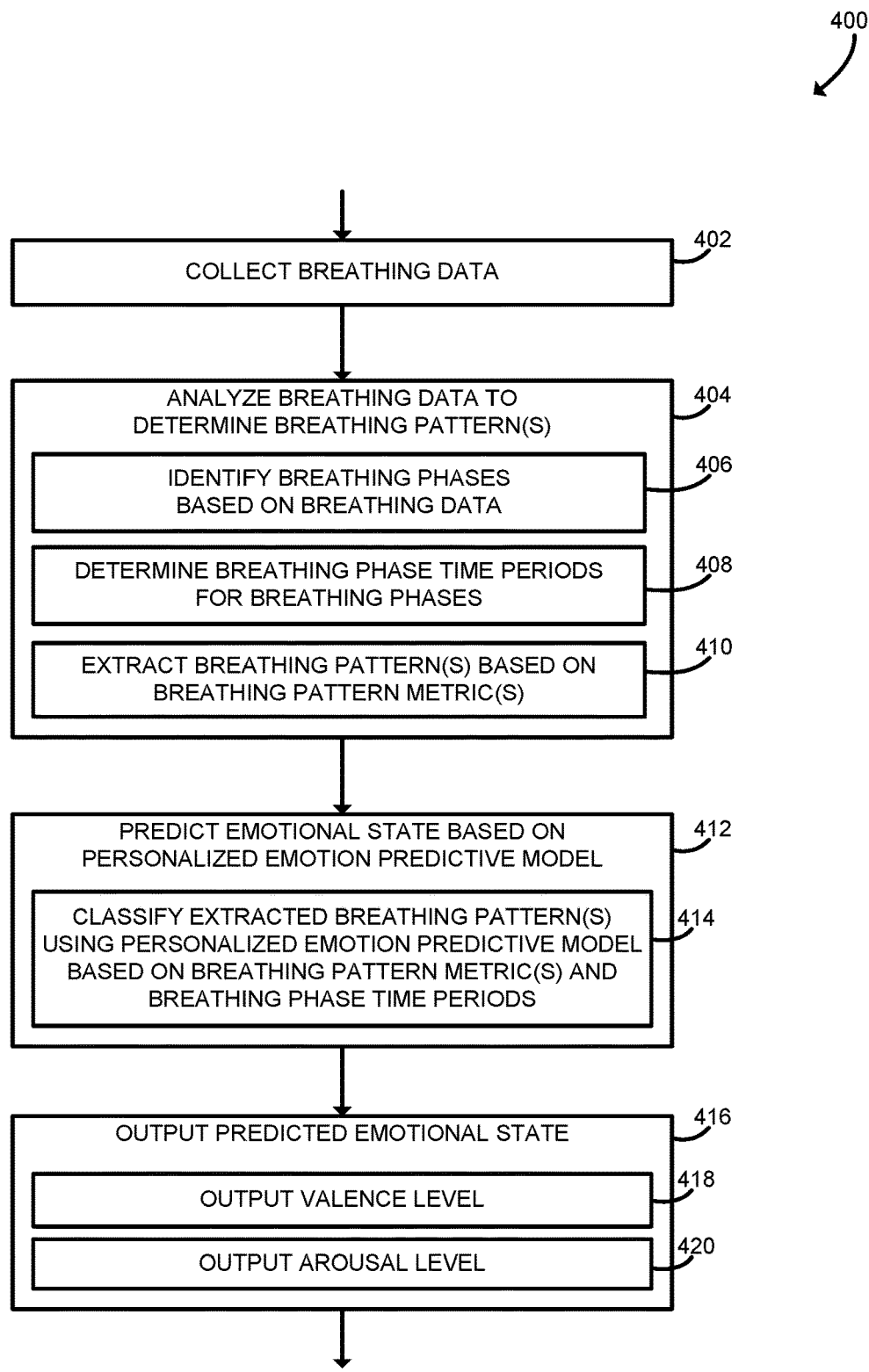
FIG. 4 is a simplified flow diagram of at least one embodiment of a method for classifying breathing patterns using a personalized emotion predictive model to predict the emotional state of a user of the wearable device that may be executed by the wearable device of FIGS. 1 and 2.

Referring now to FIG. 4, in use, the wearable device 102 may execute a method 400 for classifying breathing patterns to predict an emotional state of a user of the wearable device 102. The method 400 begins with block 402 in which the wearable device 102 collects breathing data. As described above, the breathing data is collected from one or more breathing sensors 130. While the training breathing data was collected in response to an exposure of a testing scent in block 304, in block 402, the breathing sensor(s) 130 is configured to constantly or periodically collect breathing data to continuously predict the emotional state of the user. Subsequently, in block 404, the wearable device 102 analyzes the breathing data to determine one or more breathing patterns. To do so, the wearable device 102 identifies the breathing phases based on the breathing data as indicated in block 406 and determine the breathing phase time periods for the breathing phases in block 408. In block 410, based on the breathing phase time periods, the wearable device 102 extracts breathing pattern based on one or more breathing pattern metrics. For example, the device may extract the breathing pattern similarly to the determination in the calibration method, as described above in connection with block 314. As discussed above, the breathing pattern metrics may include, among other things, a ratio between inspiration and expiration durations ($T_i/T_e$), a respiration frequency ($f_R=1/(T_i+T_{ip}+T_e+T_{ep})$), and/or ratios that indicate each phase of the respiration cycle compared to the total respiration duration ($T_i*f_R$, $T_e*f_R$, $T_{ip}*f_R$, $T_{ep}*f_R$).

Based on the extracted breathing pattern, the wearable device 102 predicts an emotional state of the user of the wearable device 102 using the personalized emotion predictive model of the user as indicated in block 412. To do so, in block 414, the wearable device 102 classifies one or more extracted breathing patterns using the personalized emotion predictive model based on the breathing pattern metrics and the breathing phase time periods ($T_i$, $T_e$, $T_{ip}$, $T_{ep}$). As described above in connection with HG. 3, the personalized emotion predictive model has been trained to classify extracted breathing patterns of the user. For example, in the illustrative embodiment, the wearable device 102 may retrieve the personalized emotion predictive model for the user of the wearable device 102 from the personalized emotion prediction model database 214 of the wearable device 102, which is located locally on the wearable device 102. It should be appreciated that the personalized emotion prediction model database 214 may be stored on the remote compute device 104. In some embodiments where there is no personalized emotion prediction model for the user of the wearable device 102 (e.g., the wearable device 102 has not been calibrated for the user), the personalized emotion predictive model may be initialized using initial model parameters locally stored in the wearable device 102. It should be appreciated that the initial parameters stored on the wearable device 102 may be generic models that have been pre-trained and are valid for a wide range of users. However, predicting an emotion of a user using a generic model is not as accurate as predicting an emotion of a user using a personalized emotion prediction model associated with the user.

In block 416, the wearable device 102 outputs a predicted emotional state of the user of the wearable device 102. For example, the wearable device 102 outputs a valence level (e.g., negative, neural, or positive) and/or an arousal level (e.g., low, medium, or high) of the user of the wearable device 102 as indicated in blocks 418 and 420, respectively. After outputting the predicted emotional state, the method 400 may loop back to block 402 to continue collecting breathing data.

It should be appreciated that, in some embodiments, the wearable device 102 may be a part of a larger affective computing system. For example, the emotional state of the user of the wearable device 102 may be shared with an external system (e.g., a virtual personal assistant such as Alexa or Siri) to give that external system an opportunity to intervene to positively change the emotional state of the user. Such intelligent agents or external systems may talk to the user and suggest activities to improve the user's mood. For example, if the user's emotion emotional state indicates that the user is in an undesirable state, such as being highly aroused with negative valence, one or more scents that have been determined to create positive emotions for the user may be provided in real-time to change the user's emotion in a desired direction. Additionally, the intelligent agents or external systems may further consider a context of a user to determine a desired target emotion. For example, for leisure time, the desired target emotion may be positive valence and low arousal; whereas for concentrated reading, the desired target emotion may be neutral or positive valence and medium arousal. The context of user may also be used to determine why the user's mood is in the predicted emotional state to provide more relevant suggestions to assist the user.

Figure 5:
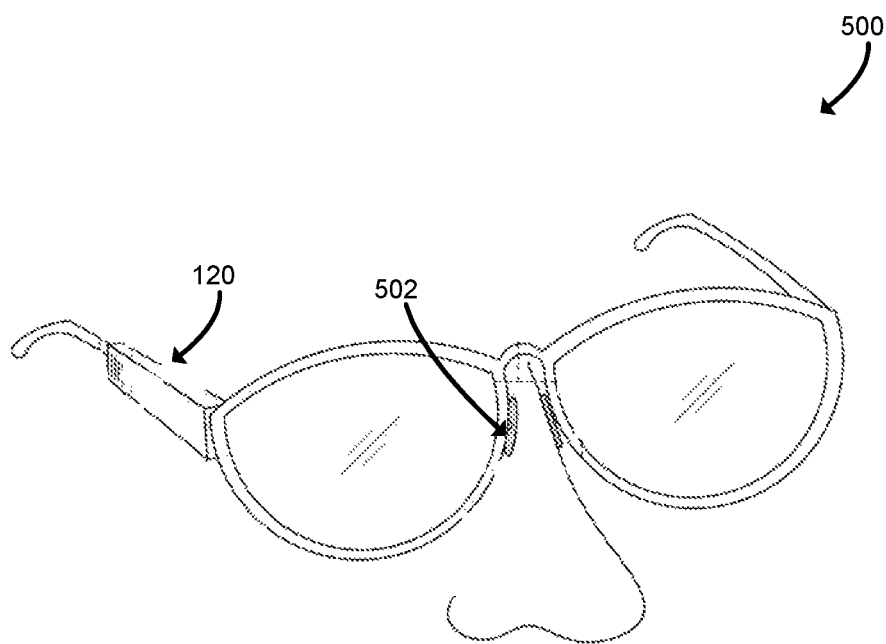
FIG. 5 is an illustration of at least one embodiment of the wearable device of FIGS. 1-4.

Referring now to FIG. 5, in the illustrative embodiment, the wearable device 102 is embodied as smart eyeglasses 500 and the breathing sensors 130 are embodied as piezoelectric sensors 502. The smart eyeglasses 500 are configured to collect breathing data via the breathing sensors 130. As shown in FIG. 5, the piezoelectric sensors 502 are positioned proximate to the nose (e.g., a bridge of a nose) of a user wearing the smart eyeglasses 500 to detect the vibration of the nasal bridge as the user breathes in and out of the user's nose and/or mouth. The piezoelectric sensors 502 are configured to produce breathing data by converting vibration into electrical signals. The breathing data is then provided to the compute engine 120, illustratively, included in a temple of the smart eyeglasses. It should be appreciated that, in some embodiments, the breathing sensor(s) 130 may be embodied as any type of sensor that can measure vibrations at other portions of the user's body (e.g., the user's temples, forehead, chest, or abdomen).

While examples of specific implementations (e.g., in eyeglasses) and/or technologies (e.g., piezoelectric sensors) are illustrated herein, these examples are presented merely to provide a readily comprehensible perspective from which the more generalized devices, systems, methods, etc. taught herein may be understood. Other applications, configurations, technologies, etc. may result in implementations that remain consistent with the teachings presented herein.

EXAMPLES

Illustrative examples of the technologies disclosed herein are provided below. An embodiment of the technologies may include any one or more, and any combination of, the examples described below.

Example 1 includes a wearable device for predicting an emotional state of a user, the wearable device comprising a breathing sensor to generate breathing data; one or more processors; and one or more memory devices having stored therein a plurality of instructions that, when executed, cause the wearable device to calibrate a personalized emotion predictive model associated with the user; collect breathing data of the user of the wearable device; analyze the breathing data to determine a breathing pattern; predict, in response to an analysis of the breathing data, the emotional state of the user using the personalized emotion predictive model; and output the emotional state of the user.

Example 2 includes the subject matter of Example 1, and wherein to calibrate the emotion predictive model comprises to collect training breathing data that corresponds to a testing scent, analyze the training breathing data to determine a breathing pattern associated with the testing scent; receive a self-labeled class indicative of an emotional state of the user in response to the testing scent; generate a user-specific class labeled data based on the breathing pattern and the self-labeled class; and create the personalized emotion predictive model for the user.

Example 3 includes the subject matter of any of Examples 1 and 2, and wherein to analyze the training breathing data to determine the breathing pattern comprises to identify breathing phases based on the training breathing data; to determine a breathing phase time period for each of the breathing phases; and to extract the breathing pattern based on breathing pattern metrics.

Example 4 includes the subject matter of any of Examples 1-3, and wherein the breathing pattern metrics include a ratio between inspiration and expiration durations, a respiration frequency, and/or ratios that indicate each phase of the respiration cycle compared to the total respiration duration.

Example 5 includes the subject matter of any of Examples 1-4, and wherein to create the personalized emotion predictive model for the user comprises to train the personalized emotion predictive model using one or more machine learning algorithms based on the user-specific class labeled data.

Example 6 includes the subject matter of any of Examples 1-5, and wherein the emotional state of the user includes a valence level.

Example 7 includes the subject matter of any of Examples 1-6, and wherein the emotional state of the user includes an arousal level.

Example 8 includes the subject matter of any of Examples 1-7, and wherein to analyze the breathing data to determine the breathing pattern comprises to identify breathing phases based on the breathing data; to determine a breathing phase time period for each of the breathing phases; and to extract breathing pattern based on breathing pattern metrics.

Example 9 includes the subject matter of any of Examples 1-8, and wherein the breathing pattern metrics include a ratio between inspiration and expiration durations, a respiration frequency, and/or ratios that indicate each phase of the respiration cycle compared to the total respiration duration.

Example 10 includes the subject matter of any of Examples 1-9, and wherein to predict the emotional state of the user using the personalized emotion predictive model comprises to classify one or more breathing patterns using the personalized emotion predictive model based on the breathing pattern metrics and the breathing phase time period for each of the breathing phases.

Example 11 includes one or more machine-readable storage media comprising a plurality of instructions stored thereon that, in response to being executed, cause a wearable device to calibrate a personalized emotion predictive model associated with the user; collect breathing data of the user from a breathing sensor of the wearable device; analyze the breathing data to determine a breathing pattern; predict, in response to an analysis of the breathing data, the emotional state of the user using the personalized emotion predictive model; and output the emotional state of the user.

Example 12 includes the subject matter of Example 11, and wherein to calibrate the emotion predictive model comprises to collect training breathing data that corresponds to a testing scent, analyze the training breathing data to determine a breathing pattern associated with the testing scent; receive a self-labeled class indicative of an emotional state of the user in response to the testing scent; generate a user-specific class labeled data based on the breathing pattern and the self-labeled class; and create the personalized emotion predictive model for the user.

Example 13 includes the subject matter of any of Examples 11 and 12, and wherein to analyze the training breathing data to determine the breathing pattern comprises to identify breathing phases based on the training breathing data; to determine a breathing phase time period for each of the breathing phases; and to extract the breathing pattern based on breathing pattern metrics.

Example 14 includes the subject matter of any of Examples 11-13, and wherein the breathing pattern metrics include a ratio between inspiration and expiration durations, a respiration frequency, and/or ratios that indicate each phase of the respiration cycle compared to the total respiration duration.

Example 15 includes the subject matter of any of Examples 11-14, and wherein to create the personalized emotion predictive model for the user comprises to train the personalized emotion predictive model using one or more machine learning algorithms based on the user-specific class labeled data.

Example 16 includes the subject matter of any of Examples 11-15, and wherein the emotional state of the user includes a valence level.

Example 17 includes the subject matter of any of Examples 11-16, and wherein the emotional state of the user includes an arousal level.

Example 18 includes the subject matter of any of Examples 11-17, and wherein to analyze the breathing data to determine the breathing pattern comprises to identify breathing phases based on the breathing data; to determine a breathing phase time period for each of the breathing phases; and to extract breathing pattern based on breathing pattern metrics.

Example 19 includes the subject matter of any of Examples 11-18, and wherein the breathing pattern metrics include a ratio between inspiration and expiration durations, a respiration frequency, and/or ratios that indicate each phase of the respiration cycle compared to the total respiration duration.

Example 20 includes the subject matter of any of Examples 11-19, and wherein to predict the emotional state of the user using the personalized emotion predictive model comprises to classify one or more breathing patterns using the personalized emotion predictive model based on the breathing pattern metrics and the breathing phase time period for each of the breathing phases.

Example 21 includes a method for predicting an emotional state of a user of a wearable device, the method comprising calibrating, by the wearable device, a personalized emotion predictive model associated with the user; collecting, by the wearable device, breathing data of the user from a breathing sensor of the wearable device; analyzing, by the wearable device, the breathing data to determine a breathing pattern; predicting, in response to an analysis of the breathing data and by the wearable device, the emotional state of the user using the personalized emotion predictive model; and outputting, by the wearable device, the emotional state of the user.

Example 22 includes the subject matter of Example 21, and wherein calibrating the emotion predictive model comprises collecting, by the wearable device, training breathing data that corresponds to a testing scent, analyzing, by the wearable device, the training breathing data to determine a breathing pattern associated with the testing scent; receiving, by the wearable device, a self-labeled class indicative of an emotional state of the user in response to the testing scent; generating, by the wearable device, a user-specific class labeled data based on the breathing pattern and the self-labeled class; and creating, by the wearable device, the personalized emotion predictive model for the user.

Example 23 includes the subject matter of any of Examples 21 and 22, and wherein analyzing the training breathing data to determine the breathing pattern comprises identifying, by the wearable device, breathing phases based on the training breathing data; determining a breathing phase time period for each of the breathing phases; and extracting the breathing pattern based on breathing pattern metrics; and creating the personalized emotion predictive model for the user comprises training, by the wearable device, the personalized emotion predictive model using one or more machine learning algorithms based on the user-specific class labeled data.

Example 24 includes the subject matter of any of Examples 21-23, and wherein analyzing the breathing data to determine the breathing pattern comprises identifying, by the wearable device, breathing phases based on the breathing data; determining a breathing phase time period for each of the breathing phases; and extracting breathing pattern based on breathing pattern metrics.

Example 25 includes the subject matter of any of Examples 21-24, and wherein predicting the emotional state of the user using the personalized emotion predictive model comprises classifying, by the wearable device, one or more breathing patterns using the personalized emotion predictive model based on the breathing pattern metrics and the breathing phase time period for each of the breathing phases.

The invention claimed is:

1. A wearable device for predicting an emotional state of a user, the wearable device comprising:
a breathing sensor to generate breathing data;
one or more processors; and
one or more memory devices having stored therein a plurality of instructions that, when executed by the one or more processors, cause the wearable device to:
collect breathing data of the user of the wearable device;
analyze the breathing data to determine a breathing pattern of the user;
calibrate a personalized emotion predictive model associated with the user, wherein the personalized emotion predictive model is based on the breathing pattern of the user associated with a testing scent;
predict, in response to an analysis of the breathing data, the emotional state of the user using the personalized emotion predictive model; and
output the emotional state of the user.

2. The wearable device of claim 1, wherein to calibrate the personalized emotion predictive model, the wearable device is to:
collect training breathing data that corresponds to the testing scent;
analyze the training breathing data to determine the breathing pattern associated with the testing scent;
receive a self-labeled class indicative of an emotional state of the user in response to the testing scent;
generate a user-specific class labeled data based on the breathing pattern and the self-labeled class; and
create the personalized emotion predictive model for the user.

3. The wearable device of claim 2, wherein to analyze the training breathing data to determine the breathing pattern, the wearable device is to:
identify breathing phases based on the training breathing data;
determine a breathing phase time period for respective ones of the breathing phases; and
extract the breathing pattern based on breathing pattern metrics.

4. The wearable device of claim 3, wherein the breathing pattern metrics include at least one of a ratio between inspiration and expiration durations, a respiration frequency, or ratios that indicate respective phases of the respiration cycle compared to the total respiration duration.

5. The wearable device of claim 2, wherein to create the personalized emotion predictive model for the user, the wearable device is to train the personalized emotion predictive model using one or more machine learning algorithms based on the user-specific class labeled data.

6. The wearable device of claim 1, wherein the emotional state of the user includes a valence level.

7. The wearable device of claim 1, wherein the emotional state of the user includes an arousal level.

8. The wearable device of claim 1, wherein to analyze the breathing data to determine the breathing pattern, the wearable device is to:
identify breathing phases based on the breathing data;
determine a breathing phase time period for respective ones of the breathing phases; and
extract breathing pattern based on breathing pattern metrics.

9. The wearable device of claim 8, wherein the breathing pattern metrics include at least one of a ratio between inspiration and expiration durations, a respiration frequency, or ratios that indicate respective phases of the respiration cycle compared to the total respiration duration.

10. The wearable device of claim 8, wherein to predict the emotional state of the user using the personalized emotion predictive model, the wearable device is to classify one or more breathing patterns using the personalized emotion predictive model based on the breathing pattern metrics and the breathing phase time period for respective ones of the breathing phases.

11. One or more machine-readable storage media comprising a plurality of instructions stored thereon that, in response to being executed, cause a wearable device to at least:
collect breathing data of a user from a breathing sensor of the wearable device;
analyze the breathing data to determine a breathing pattern;
calibrate a personalized emotion predictive model associated with the user, wherein the personalized emotion predictive model is based on the breathing pattern of the user associated with a testing scent;
predict, in response to an analysis of the breathing data, the emotional state of the user using the personalized emotion predictive model; and
output the emotional state of the user.

12. The one or more machine-readable storage media of claim 11, wherein to calibrate the personalized emotion predictive model, the instructions cause the wearable device to:
collect training breathing data that corresponds to the testing scent;
analyze the training breathing data to determine the breathing pattern associated with the testing scent;
receive a self-labeled class indicative of an emotional state of the user in response to the testing scent;
generate a user-specific class labeled data based on the breathing pattern and the self-labeled class; and
create the personalized emotion predictive model for the user.

13. The one or more machine-readable storage media of claim 12, wherein to analyze the training breathing data to determine the breathing pattern, the instructions cause the wearable device to:
identify breathing phases based on the training breathing data;
determine a breathing phase time period for respective ones of the breathing phases; and
extract the breathing pattern based on breathing pattern metrics.

14. The one or more machine-readable storage media of claim 13, wherein the breathing pattern metrics include at least one of a ratio between inspiration and expiration durations, a respiration frequency, or ratios that indicate respective phases of the respiration cycle compared to the total respiration duration.

15. The one or more machine-readable storage media of claim 12, wherein to create the personalized emotion predictive model for the user, the instructions cause the wearable device to train the personalized emotion predictive model using one or more machine learning algorithms based on the user-specific class labeled data.

16. The one or more machine-readable storage media of claim 11, wherein the emotional state of the user includes a valence level.

17. The one or more machine-readable storage media of claim 11, wherein the emotional state of the user includes an arousal level.

18. The one or more machine-readable storage media of claim 11, wherein to analyze the breathing data to determine the breathing pattern, the instructions cause the wearable device to:
 identify breathing phases based on the breathing data;
 determine a breathing phase time period for respective ones of the breathing phases; and
 extract breathing pattern based on breathing pattern metrics.

19. The one or more machine-readable storage media of claim 18, wherein the breathing pattern metrics include at least one of a ratio between inspiration and expiration durations, a respiration frequency, or ratios that indicate respective phases of the respiration cycle compared to the total respiration duration.

20. The one or more machine-readable storage media of claim 18, wherein to predict the emotional state of the user using the personalized emotion predictive model, the instructions cause the wearable device to classify one or more breathing patterns using the personalized emotion predictive model based on the breathing pattern metrics and the breathing phase time period for respective ones of the breathing phases.

21. A method for predicting an emotional state of a user of a wearable device, the method comprising:
 collecting, by the wearable device, breathing data of the user from a breathing sensor of the wearable device;
 analyzing, by the wearable device, the breathing data to determine a breathing pattern;
 calibrating, by the wearable device, a personalized emotion predictive model associated with the user, wherein the personalized emotion predictive model is based on the breathing pattern of the user associated with a testing scent;
 predicting, in response to an analysis of the breathing data and by the wearable device, the emotional state of the user using the personalized emotion predictive model; and
 outputting, by the wearable device, the emotional state of the user.

22. The method of claim 21, wherein calibrating the personalized emotion predictive model comprises:
 collecting, by the wearable device, training breathing data that corresponds to testing scent;
 analyzing, by the wearable device, the training breathing data to determine breathing pattern associated with the testing scent;
 receiving, by the wearable device, a self-labeled class indicative of an emotional state of the user in response to the testing scent;
 generating, by the wearable device, a user-specific class labeled data based on the breathing pattern and the self-labeled class; and
 creating, by the wearable device, the personalized emotion predictive model for the user.

23. The method of claim 22, wherein:
 the analyzing of the training breathing data to determine the breathing pattern includes:
  identifying, by the wearable device, breathing phases based on the training breathing data;
  determining a breathing phase time period for respective ones of the breathing phases; and
  extracting the breathing pattern based on breathing pattern metrics; and
 the creating of the personalized emotion predictive model for the user includes training, by the wearable device, the personalized emotion predictive model using one or more machine learning algorithms based on the user-specific class labeled data.

24. The method of claim 21, wherein the analyzing of the breathing data to determine the breathing pattern includes:
 identifying, by the wearable device, breathing phases based on the breathing data;
 determining a breathing phase time period for respective ones of the breathing phases; and
 extracting breathing pattern based on breathing pattern metrics.

25. The method of claim 24, wherein the predicting of the emotional state of the user using the personalized emotion predictive model includes classifying, by the wearable device, one or more breathing patterns using the personalized emotion predictive model based on the breathing pattern metrics and the breathing phase time period for respective ones of the breathing phases.

* * * * *